(12) United States Patent
La

(10) Patent No.: US 6,972,004 B2
(45) Date of Patent: Dec. 6, 2005

(54) SYRINGE FOR COLLECTING BLOOD

(76) Inventor: Keuk Hwan La, Field Com Inc., 12/6, #291-25, Yolgye-Dong, Nowon-Gu, Seoul, 139-050 (KR)

( * ) Notice: Subject to any disclaimer, the term of this patent is extended or adjusted under 35 U.S.C. 154(b) by 0 days.

(21) Appl. No.: 10/322,298

(22) Filed: Dec. 17, 2002

(65) Prior Publication Data

US 2004/0116876 A1 Jun. 17, 2004

(51) Int. Cl.⁷ .............................................. A61M 5/00
(52) U.S. Cl. ...................... 604/187; 604/227; 604/181; 222/386
(58) Field of Search ........................... 604/187, 207–8, 604/218, 220, 227, 96.01, 915, 508, 500, 604/181, 221, 228, 403; 222/386

(56) References Cited

U.S. PATENT DOCUMENTS

| 3,758,006 A | * | 9/1973 | Gravlee ...................... 222/323 |
| 4,927,416 A | * | 5/1990 | Tomkiel ..................... 604/198 |
| 5,085,640 A | * | 2/1992 | Gibbs ......................... 604/110 |
| 5,582,595 A | * | 12/1996 | Haber et al. ................ 604/187 |

* cited by examiner

*Primary Examiner*—Cris Rodriguez
(74) *Attorney, Agent, or Firm*—Cantor Colburn LLP

(57) ABSTRACT

A syringe for collecting blood includes a cylinder for sucking blood, two guide slits formed on a rear portion of the cylinder in such a way as to be symmetrical with respect to a midpoint of the guide slits, and a rod-shaped handle provided at a rear end of a piston rod in the cylinder so that the handle is transversely fitted into the guide slits. When a user puts his/her thumb on a rear end of the cylinder and rearwardly draws the handle along the guide slits using his/her index and middle fingers, blood is sucked into the cylinder by a rearward movement of the piston in the cylinder.

13 Claims, 4 Drawing Sheets

SYRINGE FOR COLLECTING BLOOD

BACKGROUND OF THE INVENTION

1. Field of the Invention

The present invention relates generally to syringes for collecting blood, and more particularly, to a syringe for collecting blood which is designed to be easily manipulated with one hand, thus allowing even an unskilled user to safely collect blood, and preventing a patient from feeling pain during a blood collecting process.

2. Description of Related Art

Generally, a syringe is a medical instrument which is used to collect blood from a patient or inject medicines into a patient. FIG. 1 is a perspective view showing a conventional syringe. Particularly, when it is required to collect blood from a patient, a user, for example, a nurse grasps the patient's arm with one hand while holding a syringe with the other hand to insert a needle 11 of the syringe into a blood vessel.

After inserting the needle 11 into the blood vessel, the user shifts his/her hand from the patient's arm to a cylinder 10 of the syringe, and rearwardly draws a piston 13 of the syringe by drawing a piston rod 14 rearward with the other hand to collect blood from the patient.

However, such a conventional syringe has a problem that it may be undesirably shaken when an unskilled user collects blood from a patient. Due to such shaking, the needle may be undesirably removed from the blood vessel of the patient, thus causing pain to the patient.

SUMMARY OF THE INVENTION

Accordingly, the present invention resolves the above problems, and provides a syringe for collecting blood which can be easily manipulated with one hand, allow even an unskilled user to safely collect blood, and prevent a patient from feeling pain during a blood collecting process.

According to one aspect of the present invention, a syringe for collecting blood, comprises a cylinder for sucking blood, two guide slits formed on a rear portion of the cylinder, the two guide slits being symmetrical with respect to a midpoint of the guide slits, and a rod-shaped handle provided at a rear end of a piston rod in the cylinder so that the handle is transversely fitted into the guide slits. When a user puts his/or her thumb on a rear end of the cylinder and rearwardly draws the handle along the guide slits using his/her index and middle fingers, blood is sucked into the cylinder by a rearward movement of the piston in the cylinder.

According to the present invention, the guide slits are axially provided on the cylinder, and comprise open rear ends so that the handle is inserted into the guide slits, thus being mounted to the cylinder. The guide slits are axially provided on the cylinder such that the guide slits are bent at their center portions, and the guide slits comprise open rear ends so that the handle is inserted into the guide slits, thus being mounted to the cylinder.

Further, the syringe further comprises an end cap covering the rear end of the cylinder, and the end cap comprises a fitting groove so that an edge of the rear end of the cylinder is fitted into the fitting groove.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF PREFERRED EMBODIMENTS

Figure 1:
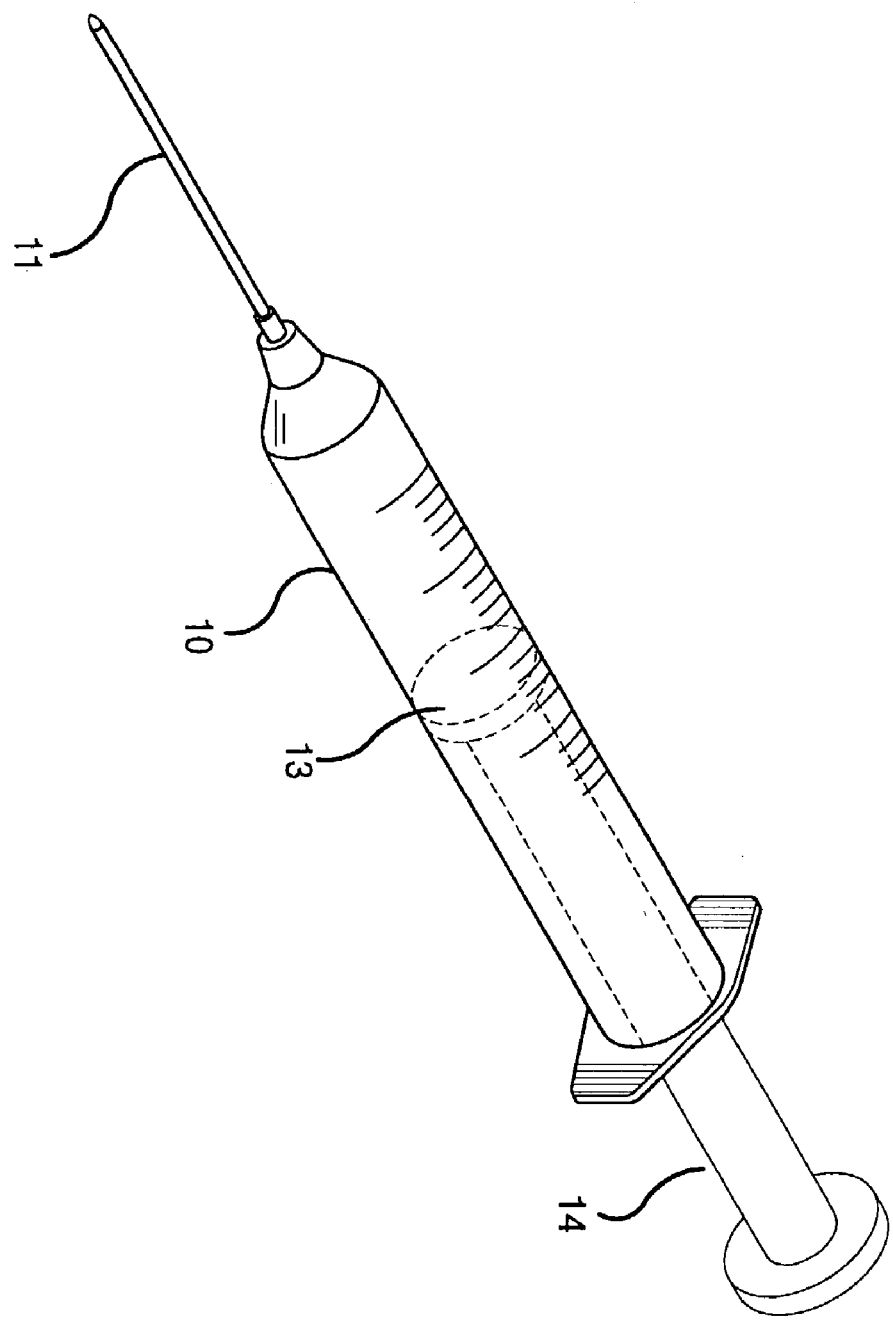
FIG. 1 is a perspective view showing a conventional syringe.

Reference should now be made to the drawings, in which the same reference numerals are used throughout the different drawings to designate the same or similar components.

Figure 2:
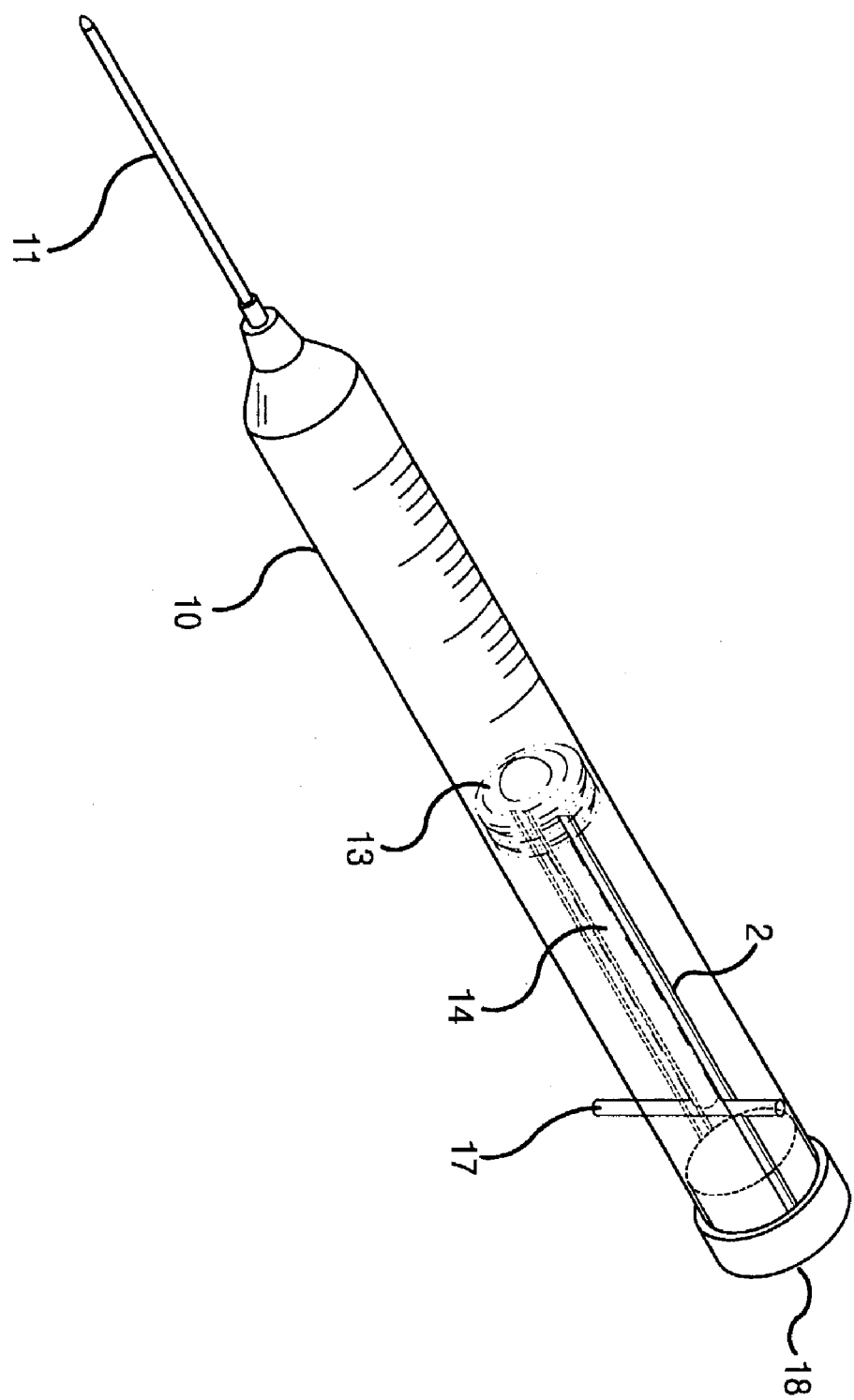
FIG. 2 is a perspective view showing a syringe according to an exemplary embodiment of the present invention.

As shown in FIG. 2, the syringe according to an exemplary embodiment of the present invention includes a cylinder 10, and two guide slits 2. The two guide slits 2 are formed on a rear portion of the sidewall of the cylinder 10 and are formed at diametrically opposite positions of the rear portion such that the guide slits are symmetrical with respect to a midpoint therebetween.

The guide slits 2 are axially and longitudinally formed on the cylinder 10. Each of the guide slits 2 has a closed front end and an open rear end.

A rod-shaped handle 17 is mounted to a rear end of a piston rod 14. The handle 17 is fitted into the open rear ends of the guide slits 2, and then is pushed forward along the guide slits 2, thus being transversely set in the guide slits 2.

When the handle 17 is mounted to the cylinder 10 in this way, the handle 17 is outwardly projected at its both ends from the cylinder 10. In such a state, when a user pulls the handle 17 rearward using his/her index and middle fingers, the handle 17 moves rearward along the guide slits 2, thus rearwardly moving a piston 13.

According to the present invention, the syringe also includes an end cap 18 which covers an open rear end of the cylinder 10. The end cap 18 is provided with a fitting groove 18-1 (referring to FIG. 3) so that an edge of the open rear end of the cylinder 10 is fitted into the fitting groove 18-1, thus preventing the rear end of the cylinder 10 from undesirably expanding in a radial direction due to the guide slits 2 which are formed on the cylinder 10.

The end cap 18 provides a thumb contact surface, thus preventing the syringe from shaking when collecting blood from a patient.

Further, the end cap 18 closes the open rear ends of the guide slits 2, thus is preventing the handle 17 from being unexpectedly removed from the guide slits 2 when the handle 17 moves rearward to collect blood from a patient.

Figure 3:
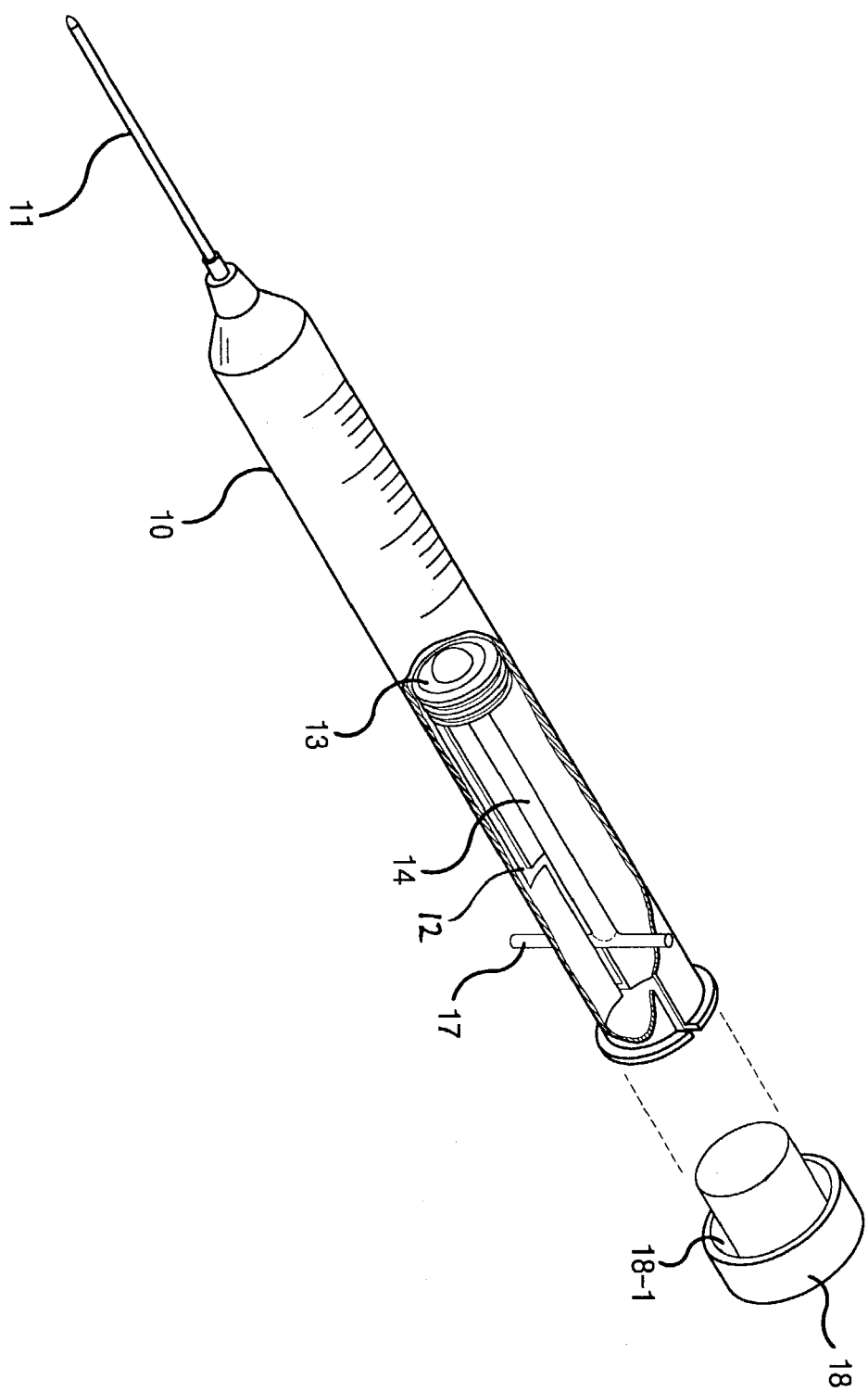
FIG. 3 is a partially-broken perspective view showing a syringe according to another exemplary embodiment of the present invention.

Meanwhile, as shown in FIG. 3, the syringe according to another exemplary embodiment of the present invention includes a cylinder 10. Two guide slits 12 are formed on a rear portion of the sidewall of the cylinder 10 and formed at diametrically opposite positions such that the two guide slits 12 are symmetrical with respect to a midpoint therebetween.

The guide slits 12 are axially and longitudinally formed along the cylinder 10. Each of the guide slits 12 has a closed front end and an open rear end. In the embodiment, the guide slits 12 are different from the guide slits 2 of FIG. 2 in that each of the guide slits 12 is bent at its center portion.

A rod-shaped handle 17 is mounted to a rear end of a piston rod 14. In order to movably mount the handle 17 to the cylinder 10, the handle 17 is fitted into the open rear ends of the guide slits 12, and then is pushed forward. While the handle 17 moves forward as such, the handle 17 is rotated at the bent portions which are formed at the center portions of the guide slits 12.

Since the guide slits 12 are bent at their center portions, the handle 17 is stopped at the bent center portions while moving rearward. Thus, the bent portions serve as a stopper which limits a rearward movement of the handle 17.

That is, when the bent portions are formed on the guide slits 12 at predetermined positions according to the amount of blood to be collected, a desired amount of blood is easily collected by a rearward movement of the piston 13 because the handle 17 is stopped at the bent portions of the guide slits 12.

Figure 4:
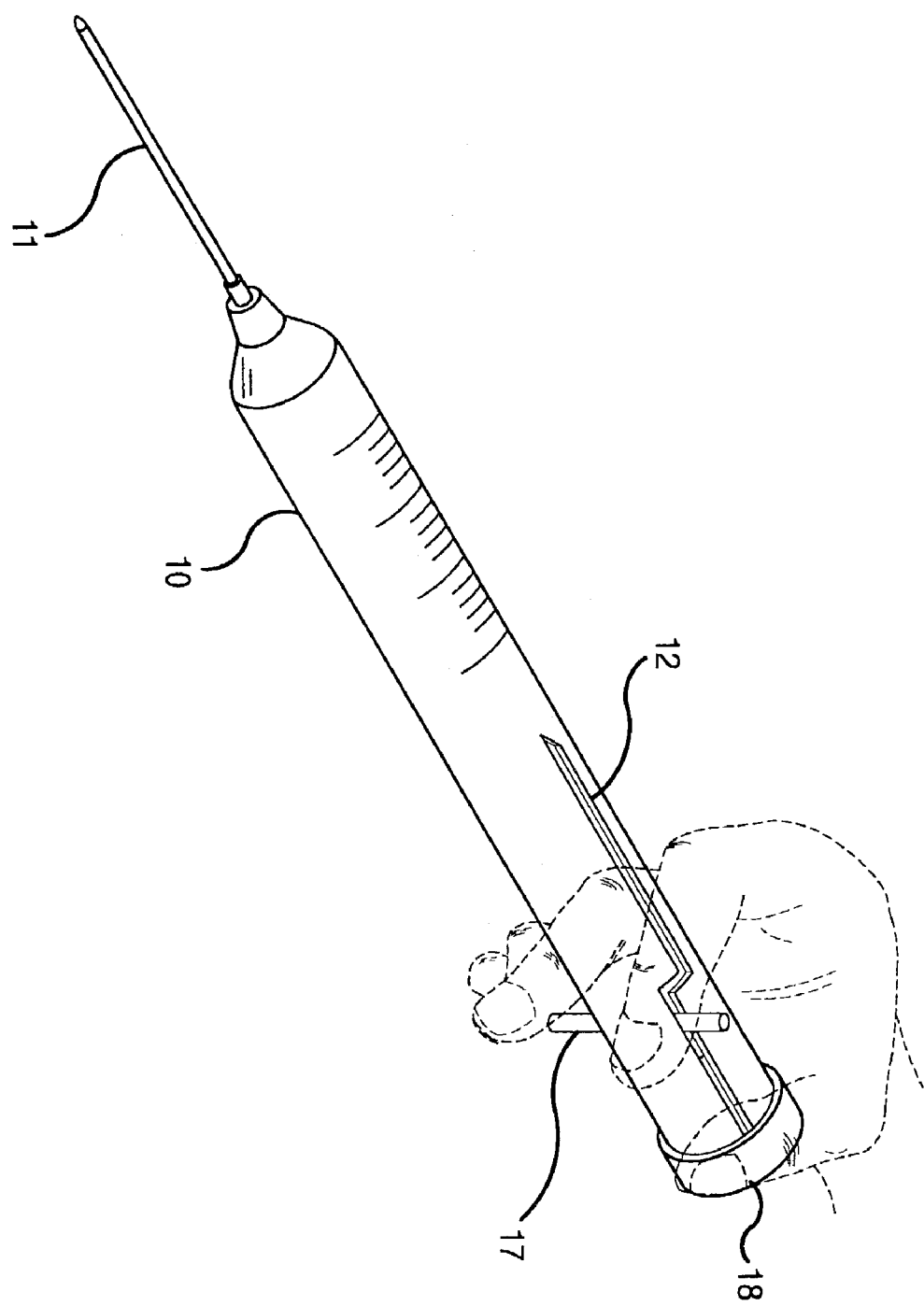
FIG. 4 is a view showing the syringe of FIG. 3, when the syringe is used to collect blood from a patient.

The operation of the syringe according to the present invention is as follows. As shown in FIG. 4, at the initial stage, the handle 17 is positioned at the front ends of the guide slits 2 or 12. At this time, the piston 13 is placed at a foremost position in the cylinder 10.

In such a state, a user grasps a patient's arm with a hand while grasping the syringe with the other hand. When grasping the syringe, the user puts his/her thumb on the end cap 18. The user also puts his/her index and middle fingers on the front portion of the cylinder 10 in front of the handle 17 in such a way as to stably hold the cylinder 10 while being in contact with both projecting ends of the handle 17.

Next, the needle 11 is inserted into the blood vessel of the patient. Subsequently, when the handle 17 is moved rearward along the guide slits 2 or 12 by the user's index and middle fingers, the piston 13 moves rearward along the inner surface of the cylinder 10, thus sucking blood into the cylinder 10 from the patient through the needle 11 which is inserted into the blood vessel.

As such, shaking of the syringe of the present invention is minimized even when an unskilled user collects blood from the blood vessel of a patient, and a blood collecting process is completed within a short period of time, thus preventing the patient from feeling pain.

As described above, the present invention provides a syringe for collecting blood, which is designed to be easily manipulated with a single hand, allows blood to be collected within a short period of time, prevents a needle of the syringe from shaking, thus preventing a patient from feeling pain during a blood collecting process and allowing even an unskilled user to easily and safely collect blood, therefore being widely used to collect blood from patients in various places, such as a hospital.

Although exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A syringe for collecting blood, comprising:
   a cylinder for sucking blood;
   two guide slits formed on a rear portion of the cylinder, the guide slits being symmetrical with respect to a midpoint of the guide slits; and
   a rod-shaped handle provided at a rear end of a piston rod in the cylinder so that the handle is transversely fitted into the guide slits,
   wherein the guide slits each have at least one stopper at a selected position of the respective guide slits, the guide slits each having a bent portion at the stopper such that the rod-shaped handle is stopped by the stopper when moving toward a rear end of the cylinder, the guide slits extending from the rear end of the cylinder toward a forward end of the cylinder in an longitudinal direction, the guide slits extending in a circumferential direction at the bent portion.

2. The syringe according to claim 1, wherein each of the guide slits comprises an open rear end so that the handle is inserted into the guide slits and is mounted to the cylinder.

3. The syringe according to claim 2, wherein each of the guide slits comprises a closed front end.

4. The syringe according to claim 1, further comprising an end cap for covering a rear end of the cylinder.

5. The syringe according to claim 4, wherein the end cap comprises a fitting groove receiving an edge of the rear end of the cylinder.

6. The syringe according to claim 1, wherein when a user puts his/her thumb on a rear end of the cylinder and rearwardly draws the handle along the guide slits using his/her index and middle fingers, blood is sucked into the cylinder by a rearward movement of the piston in the cylinder.

7. The syringe according to claim 1, wherein the handle is integrally provided at a rear end of the piston rod such that the handle and the piston rod form a "T" shape.

8. A syringe for collecting blood, comprising:
   a cylinder for receiving blood;
   two guide slits formed on a rear portion of the cylinder, the guide slits being symmetrical with respect to a midpoint of the guide slits, the guide slits penetrating entirely through a sidewall of the cylinder, the guide slits each including a first section and a second section extending in a longitudinal direction of the cylinder; and
   a rod-shaped handle provided at a rear end of a piston rod disposed in the cylinder so that the rod-shaped handle is transversely fitted into the guide slits and opposite ends of the mid-shaped handle protrude through the guide slits to an exterior of the cylinder,
   wherein the guide slits each include a stopper at a selected position of the guide slits, the guide slits each having a bent portion forming the stopper such that the rod-shaped handle is stopped by the stopper when moving toward a rear end of the cylinder, the guide slits extending in a circumferential direction at the bent portion, the bent portion being disposed between the first and second sections, and the rod-shaped handle rotatable at the bent portion such that movement of the rod-shaped handle over an entire range of the guide slits requires movement in the longitudinal direction through the first and second section and rotation in the circumferential direction through the bent portion.

9. The syringe according to claim 8, wherein each of the guide slits comprises an open rear end so that the handle is inserted into the guide slits and is mounted to the cylinder.

10. The syringe according to claim 9, wherein each of the guide slits comprises a closed front end.

11. The syringe according to claim 8, further comprising an end cap for covering a rear end of the cylinder.

12. The syringe according to claim 11, wherein the end cap comprises a fitting groove receiving an edge of the rear end of the cylinder.

13. The syringe according to claim 8, wherein the handle is integrally provided at a rear end of the piston rod such that the handle and the piston rod form a "T" shape.

* * * * *